United States Patent [19]

Ford et al.

[11] Patent Number: 5,411,929
[45] Date of Patent: May 2, 1995

[54] THERMALLY-PROCESSABLE IMAGE RECORDING MATERIALS INCLUDING SUBSTITUTED PURINE COMPOUNDS

[75] Inventors: Maureen F. Ford, Cambridge; Donna J. Guarrera, Norwood; Mark R. Mischke, Arlington; Ramdas P. Pai, Roslindale; John C. Warner, Norwood, all of Mass.

[73] Assignee: Polaroid Corporation, Cambridge, Mass.

[21] Appl. No.: 269,925

[22] Filed: Jun. 30, 1994

[51] Int. Cl.⁶ .................. B41M 5/30; C07D 311/00; C07D 495/10; G03C 1/73
[52] U.S. Cl. ................................. 503/210; 430/332; 430/338; 430/341; 430/343; 430/348; 430/620; 430/964; 503/209; 503/216; 503/217; 503/220; 503/224
[58] Field of Search ................. 427/150–152; 430/332, 338, 341, 343, 348, 620, 964; 503/209, 210, 215–217, 220, 224, 225

[56] References Cited

U.S. PATENT DOCUMENTS

| | | | |
|---|---|---|---|
| 3,615,616 | 10/1971 | Willems et al. | 96/109 |
| 3,785,814 | 1/1974 | Land et al. | 96/3 |
| 3,801,318 | 4/1974 | Land et al. | 96/3 |
| 4,170,480 | 10/1979 | Ikenoue et al. | 96/114.1 |
| 4,521,793 | 6/1985 | Kabashima et al. | 503/201 |
| 4,904,572 | 2/1990 | Dombrowski, Jr. et al. | 430/332 |
| 4,970,309 | 11/1990 | King | 544/278 |
| 5,028,725 | 7/1991 | King | 556/113 |
| 5,196,297 | 3/1993 | Dombrowski, Jr. et al. | 430/338 |
| 5,198,406 | 3/1993 | Mack et al. | 503/207 |
| 5,220,036 | 6/1993 | King | 549/52 |
| 5,278,127 | 1/1994 | Dombrowski et al. | 503/207 |

FOREIGN PATENT DOCUMENTS 0250558  5/1990  European Pat. Off. ............ 503/220

Primary Examiner—B. Hamilton Hess
Attorney, Agent, or Firm—Edward W. Black

[57] ABSTRACT

There are disclosed thermally-processable image recording materials comprising a support carrying thereon; a di- or triarylmethane thiolactone dye, an organic silver salt, a binder; and a select group of substituted purine compounds for reducing a post-processed formation of a yellowish-brown color (gilding) within such materials.

13 Claims, No Drawings

THERMALLY-PROCESSABLE IMAGE RECORDING MATERIALS INCLUDING SUBSTITUTED PURINE COMPOUNDS

BACKGROUND OF THE INVENTION (1) Field of the Invention

The present invention generally relates to thermally-processable image recording materials including a di- or triarylmethane thiolactone dye precursor, an organic silver salt, and a binder. More particularly, the present invention is directed toward such image recording materials which further include a particular substituted purine compound.

(2) Description of the Related Art

Thermally-processable image recording materials utilizing di- and triarylmethane thiolactone dye precursors and an organic silver salt are known in the art. Examples of such image recording materials are provided in U.S. Pat. Nos. 4,904,572; 5,196,297; 5,198,406; and 5,278,127; all assigned to the assignee of the present invention. Further examples are provided in European Patent Application 250,558. In thermographic embodiments of such materials, images are typically formed by image-wise heating of the media, whereas in photothermographic embodiments, the image recording materials are initially exposed to light followed by thermal processing. Processing typically involves only heating and does not usually require treatment with water or any other liquids.

After processing, such image recording materials may exhibit a progressive formation of a yellowish-brown color, particularly noticeable after prolonged exposure to light. Although not fully understood, it is believed that this progressive color formation, hereinafter referred to as "gilding", is due to a silver photolysis process causing a bulk-scale reduction of non-photosensitive silver. The gilding process should be distinguished from phenomena such as fog, which is generally attributed to development of unexposed photosensitive silver. Fog and problems associated with instability of photosensitive silver are addressed by the prior art. For example, U.S. Pat. No. 4,170,480 discloses a photothermographic material which includes a 1,2,4-triazole compound for decreasing fog associated with photosensitive silver. Similarly, U.S. Pat. Nos. 3,615,616; 3,801,318 and 3,785,814 describe compounds for reducing fog in photographic materials. More specifically, U.S. Pat. No. 3,615,616 describes a photographic material including a photosensitive silver halide and a bistetrazole compound for decreasing fog. U.S. Pat. Nos. 3,785,814 and 3,801,318 disclose a photographic diffusion transfer material which utilizes a substituted purine as a silver halide complexing agent in combination with a silver halide solvent, for decreasing fog.

SUMMARY OF THE INVENTION

The present invention is a thermally-processable image recording material comprising a support carrying: a di- or triarylmethane thiolactone dye precursor, an organic silver salt, a binder, and a substituted purine compound represented by the formula:

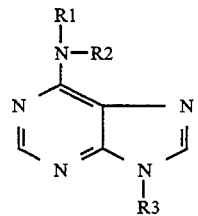

Formula 1 wherein R1, R2, and R3 are substituents which render the purine compound mobile within the image recording material, and provided at least one of R1, R2, and R3 is hydrogen. The image recording materials of the present invention exhibit reduced gilding, particularly after prolonged exposure to ambient light.

DETAILED DESCRIPTION OF THE INVENTION

The present invention is a thermally-processable image recording material comprising a di- or triarylmethane thiolactone dye precursor, a substantially non-photosensitive organic silver salt, a binder material and a substituted purine compound, as will be described in detail. The subject image recording material, (media) includes both thermographic and photothermographic embodiments as described below.

The image recording media of the present invention includes a select group of substituted purine compounds which can be represented by the formula:

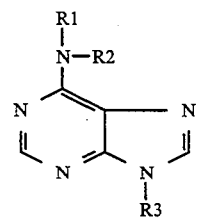

Formula 1 wherein R1, R2, and R3 are substituents which render the purine compound mobile within the image recording material, and provided at least one of R1, R2, and R3 is hydrogen. More particularly, R1, R2, and R3 are groups which permit the purine compound to diffuse, i.e. move through and about, within the image recording media. At a minimum, this requires that the substituted purine compound be substantially non-reactive (inert) with the binder or binder system of the media and to be diffusible or mobile therein. The term "substantially non-reactive" is intended to include trace chemical reactions between the binder and substituted purine which have no substantive effect or impact upon the media system. Examples of suitable substituents include: amide; amine; alkylthio; alkoxy; hydrogen; hydroxy; aliphatic groups e.g. alkyl, alkenyl; acyl (carbonylalkyl), non-aromatic cyclic structures e.g. cyclopropyl, pyrrole, imidazolidine; and aromatic ring structures e.g. phenyl, naphthyl, pyridinyl, furanyl, pyrazinyl, etc. The substituents R1, R2, and R3 may be substituted with further substituents, including hydroxy, alkyl, amide, amine, etc., so long as the purine compound remains mobile within the image-recording material.

As previously stated, although not fully understood, it is believed that the gilding effect is attributed to a silver photolysis process. Furthermore, it is believed that the subject substituted purine compounds form complexes with silver within the imaging media which reduces perceived gilding. As such, it is believed to be further beneficial if R1, R2, and R3 are substituents which permit the purine compound to form complexes with silver, within the image recording media. Thus, in addition to being mobile in the imaging media, it preferred that the substituents R1, R2, and R3, permit the purine compound to form silver complexes with the silver within the media. Preferably, R1, R2 and R3 are selected from the group consisting of: hydrogen, aliphatic (e.g. alkyl, vinylic), alkaryl (e.g. benzyl, ethylpyridyl), and acyl (e.g. carbonylalkyl). More preferably, R1 is selected from hydrogen, alkyl comprising from 1 to 20 carbon atoms, and alkaryl, R2 is selected from alkaryl, and R3 is selected from hydrogen and acyl (carbonylalkyl wherein the alkyl portion comprises from 1 to 20 carbon atoms). Examples of substituted purine compounds within the scope of the present invention include: 9-lauroyl-6-benzylaminopurine; 9-acetyl-6-benzylaminopurine; 9-propionyl-6-benzylaminopurine; 9-butyroyl-6-benzylaminopurine; 6-(N,N-dibenzylamino)purine; 6-(N-methyl-N-benzylamino)purine; 6-(2-pyridylmethylamino)purine; 6-benzylaminopurine; and 6-dodecylaminopurine. The aforementioned purine compounds are commercially available from the Aldrich Chemical Co. or can be readily synthesized from 6-chloropurine as generally described in Bullock, M. W.; Hand, J. J.; Stokstad, E. L. R. *Journal of the American Chemical Society*, 78, p 3693, (1956).

The organic silver salts of the present invention include silver salts of long chain aliphatic carboxylic acids such as silver laurate, silver myristate, silver palmitate, silver stearate, silver arachidate and silver behenate; silver salts of organic compounds having an imino group such as benzotriazole silver salt, benzimidazole silver salt, carbazole silver salt and phthalazin one silver salt; silver salts of sulfur containing compounds; silver salts of aromatic carboxylic acids such as silver benzoate and silver phthalate; silver salts of sulfonic acids such as silver ethanesulfonate; silver salt of sulfinic acids such as silver o-toluenesulfinate; silver salts of phosphoric acids such as silver phenylphosphate; silver barbiturate; silver saccharate; silver salts of salicylaldoxime; and any mixtures thereof. Of these compounds, silver salts of long chain aliphatic carboxylic acids are preferred and particularly, silver behenate which may be used in admixture with other organic silver salts if desired. Also, behenic acid may be used with the silver behenate.

The organic silver salts of the present invention are preferably substantially non-photosensitive. That is, the preferred silver salts are not capable of forming discernable photo images without the addition of a photosensitive material such as a conventional photosensitive silver halide.

The preparation of the subject organic silver salts is generally carried out by processes which comprise mixing a silver salt forming organic compound dispersed or dissolved in a suitable liquid with an aqueous solution of a silver salt such as silver nitrate or a silver complex salt. Various procedures for preparing the organic silver salts are described in U.S. Pat. Nos. 3,458,544, 4,028,129 and 4,273,723.

The individual components of the subject image recording material can be coated on a variety of supports to provide images on one or both sides of the support. Depending upon whether the image is to be viewed by transmission or reflection, the support may be transparent or opaque. Useful supports are those that retain their dimensional stability at processing temperatures and are resistant to the solvent employed in applying the image recording layers to the support. Typical supports include paper, paper coated with baryta, polyethylene or other pigment or resin, metal foils and plastic films such as cellulose acetate, polyethylene, polypropylene, polycarbonate and polyethylene terephthalate. Specific examples of suitable reflective supports include polyethylene clad paper such as that sold by Glory Mill Papers Limited (type 381), Glory Paper Mill, Wooburn Green, Wylombe, Buckingham Shire, England HP10 0DB; and Baryta coated paper such as that sold by Sehoeller Technical Papers Inc. (type 527), Pulaski, N.Y. 13142-0250. Specific examples of suitable transparent supports include polypropylene, cellulose acetate, and most preferably, polyethylene terephthalate substrate commercially available from ICI Americas, Inc., Wilmington, Del. The thickness of the support is not particularly restricted, but should generally be in the range of about 2 to 10 mils. The support may be pretreated to enhance adhesion of the polymeric coating thereto.

Di- and triarylmethane thiolactone dye precursors particularly useful in the imaging systems in accordance with this invention are disclosed in U.S. Pat. Nos. 5,220,036; 5,028,725 and 4,970,309, and are incorporated herein by reference. Preferred dye precursors may be represented by Formula 2 provided below;

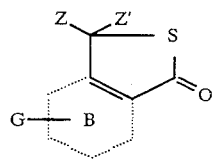

Formula 2 wherein ring B represents a substituted or unsubstituted carbocyclic aryl ring or rings, e.g., of the benzene or naphthalene series or a heterocyclic ring, e.g., pyridine or pyrimidine; G is hydrogen or a monovalent radical; and Z and Z' taken individually represent the moieties to complete the auxochromophoric system of a diarylmethane or a triarylmethane dye when said S-containing ring is open and Z and Z' taken together represent the bridged moieties to complete the auxochromophoric system of a bridged triarylmethane dye when said S-containing ring is open, i.e., when the ring sulfur atom is not bonded to the meso carbon atom. Usually, at least one of Z and Z' whether taken individually or together possesses as an auxochromic substituent, a nitrogen, oxygen or sulfur atom or a group of atoms containing nitrogen, oxygen or sulfur.

In a preferred embodiment, B is a benzene ring and Z and Z' taken individually or together complete the auxochromophoric system of a triarylmethane dye.

The dye precursor compounds used in the present invention can be monomeric or polymeric compounds. Suitable polymeric compounds are those which, for example, comprise a polymeric backbone chain having dye precursor moieties attached directly thereto or through pendant linking groups. Polymeric compounds of the invention can be provided by attachment of the dye precursor moiety to the polymeric chain via the Z and/or Z' moieties or the ring B. For example, a monomeric dye precursor compound having a reachable substituent group, such as an hydroxyl or amino group, can be conveniently reacted with a monoethylenically unsaturated, polymerizable compound having a functional and derivatizable moiety, to provide a polymerizable monomer having a pendant dye precursor moiety. Suitable monoethylenically unsaturated compounds for this purpose include acryl chloride, methacryl chloride, methacrylic anhydride, 2-isocyanatoethyl methacrylate and 2-hydroxyethyl acrylate, which can be reacted with an appropriately substituted dye precursor compound for production of a polymerizable monomer which in turn can be polymerized in known manner to provide a polymer having the dye precursor compound pendant from the backbone chain thereof.

The thiolactone dye precursors can be synthesized, for example, from the corresponding lactones by heating substantially equimolar amounts of the lactone and phosphorus pentasulfide or its equivalent in a suitable solvent. For further information regarding the synthesis of thiolactone dye precursors, reference is made to the aforementioned U.S. Pat. Nos. 5,220,036; 4,970,309 and 5,028,725.

In addition to the dye precursor and organic silver salt, the system preferably includes an organic acid material which upon heating to processing temperatures, provides an improved reaction medium for facilitating contacting and reaction of the dye precursor and the silver (of the organic silver salt) to produce the dye image. The acid material is typically a phenol or an organic carboxylic acid, particularly a hydroxy-substituted aromatic carboxylic acid. Examples of useful acid materials are disclosed in U.S. Pat. Nos. 5,196,297 and 4,904,572 which are incorporated herein by reference. It will be appreciated that the particular organic acid material selected will depend upon the processing temperatures employed and upon the dye precursor and that it may be selected empirically on the basis of relative performance in giving dye images having the desired maximum and minimum densities for a given image recording system and the desired image stability. A single organic acid can be employed or a combination of two or more may be used.

The binder of the present invention may consist of any known binder material used in thermographic and photothermographic materials. Furthermore, the binder may consist of a binder system formed by the combination of a plurality of individual binder materials. The binder is inert, i.e., does not have any adverse effect on other constituents of the image recording media. Also, the binder should be heat-stable at processing temperatures and is preferably transparent so that it does not interfere with viewing of the image. The choice of binder is also governed by the choice of the other components especially the substituted purine compound and the organic silver salt, as will be described. Suitable binders include hydrophobic binders such as polyvinyl butyral, cellulose acetate and ethyl cellulose; and hydrophilic binders such as gelatine, polyvinyl alcohol and hydroxyethylcellulose.

The processing of the subject image recording materials is preferably dry. The term "dry" as used herein is intended to mean that neither water nor other treatment liquids are directly added to the system during processing or for the purpose of processing; however, the system may be in a state of equilibrium with moisture in the air. Such a state is described in T. H. James (ed.), *The Theory of the Photographic Process,* 4th Ed., Macmillan (1977), pg. 374. Thus, the term "dry" is intended to include instances where trace amounts of liquids are present in the media but which have no substantial effect. Furthermore, the term "dry" is not intended to limit the process for making the subject image recording material. That is, water or other liquids may be used as solvents or dispersant in order to prepare and/or coat the various constituents of the image recording material, however, any such liquid must be removed, (e.g. by drying), prior to imaging.

The dye precursor and silver salt may be used as solids or one or both may be encapsulated and contained in a single sheet in the same or different layers or contained in separate superposed sheets, and color formation brought about in an imagewise fashion by the imagewise application of heat to effect imagewise contact between the two components. In systems employing two sheets, the dye precursor may be coated in a binder on one sheet and the silver salt coated in a binder on the other and heat applied imagewise to the superposed sheets to effect melting and contact of the two components.

As stated, the dye precursor and silver salt may be contained in the same sheet, that is, a single support carrying both the dye precursor and the silver salt. In a particularly preferred embodiment, an image recording material comprises a support carrying a di- or triarylmethane thiolactone dye precursor, an organic silver salt and optionally, a heat-fusible organic acidic material. For photothermographic use, the image recording material additionally includes in catalytic association with the organic silver salt, a photosensitive silver halide or a photosensitive silver halide-forming component and a reducing agent. Preferably, the dye precursor is a triarylmethane thiolactone, particularly, a thiophthalide, the organic silver salt is silver behenate, and the acid material is 3,5-dihydroxybenzoic acid.

Where the dye precursor and organic silver salt are contained in separate sheets, the acid material usually is associated with the organic silver salt. Where the dye precursor and organic silver salt are contained in the same sheet, they may be in the same or different layers on the same or different sides of a support. The heat-fusible organic acidic material may be in the same layer as the dye precursor and/or organic silver salt or in a separate layer. For example, the organic acidic material and organic silver salt may be disposed in one layer and the dye precursor in an adjacent layer or the dye precursor and organic silver salt may be disposed in one layer and the organic acidic material in an adjacent layer. Alternatively, all three components may be contained in the same layer.

Whether in the same or different layers, the dye precursor, organic silver salt and organic acidic material are usually dispersed in a binder which is inert, i.e., does not have any adverse effect on the dye precursor. Also, the binder should be heat-stable at processing temperatures and is preferably transparent so that it does not interfere with viewing of the color image. Besides being inert with respect to the dye precursor, the choice of binder is also governed by the choice of the other components especially the substituted purine compound and the organic silver salt. As previously stated, the substituted purine compound should be diffusible in the binder or binder system. The binder may be a hydrophilic binder such as gelatin, polyvinyl alcohol or hydroxyethylcellulose, or may be a hydrophobic binder such as polyvinyl butyral, cellulose acetate or ethyl cellulose.

The layer or layers of the above-mentioned imaging components can be coated on a variety of supports to provide images on one or both sides of the support. Depending upon whether the color image is to be viewed by transmission or reflection, the support may be transparent or opaque.

A method of thermal imaging using the above-described thermographic recording materials includes the steps of imagewise heating a recording element which comprises a support carrying at least one layer comprising (a) at least one dye precursor compound having associated therewith in the same or a different layer (b) an organic silver salt and optionally, (c) a heat-fusible organic acidic material. The step of imagewise heating provides an imagewise distribution of $Ag^+$ for reaction with the dye precursor compound whereby color is formed in an imagewise pattern corresponding to the imagewise heating. Heat may be applied or induced imagewise in a variety of ways, for example, by direct application of heat using a thermal printing head or thermal recording pen, by conduction from heated image-markings of an original using conventional thermally-processable copying techniques or by heat generated in response to an electric signal by including, e.g., an electroconductive material or a resistive layer. Also, selective heating may be produced in the image-forming layer(s) by the conversion of electromagnetic radiation into heat. Preferably, the light source is a laser beam emitting source such as a gas laser or semiconductor laser diode.

In the latter embodiment an infra red absorbing substance is employed for converting infra red radiation into heat for providing an imagewise distribution of $Ag+$ for effecting imagewise color formation. Preferably, the infra red absorber is an organic compound such as a cyanine, merocyanine or thiopyrylium dye and preferably, it is substantially non-absorbing in the visible region of the electromagnetic spectrum so that it will not add any substantial amount of color to the $D_{min}$ areas, i.e., the highlight areas of the dye image.

In a further embodiment, multicolor images may be produced using the same infra red absorbing compound in association with each of two or more sets of color-forming components and exposing each by controlling the depth of focussing of the laser beam. In this embodiment, the concentration of infra red absorber is adjusted so that each of the infra red absorbing layers absorb approximately the same amount of laser beam energy. For example, where there are three infra red absorbing layers, each layer would absorb about one-third of the laser beam energy. It will be appreciated that controlling the focussing depth to address each layer separately may be carried out in combination with the previous embodiment of using infra red absorbers that selectively absorb at different wavelengths in which instance the concentration of infra red absorber would not have to be adjusted for the laser beam energy since the first infra red dye would not absorb any substantial amount of radiation at the absorption peaks of the second and third dyes and so forth.

Where imagewise heating is induced by converting light to heat as described above, the heat-sensitive element comprising the dye precursor/organic silver salt for providing either monochrome or multicolor images may be heated prior to or during imagewise heating. This may be achieved using a heating platen or heated drum or by employing an additional laser beam source for heating the element while it is being exposed imagewise.

As noted above, the dye precursor and organic silver salt may be carried on the same or on separate supports. In the production of multicolor images, they are usually carried on the same support and preferably are contained in the same layer which preferably also includes the organic acidic material. Where electromagnetic radiation using, for example, a laser source is employed to induce imagewise heating as discussed above, the binder used for the imaging layers should transmit the light intended to bring about image formation.

In a further embodiment, a photosensitive material together with a reducing agent may be included with the organic silver salt and dye precursor to provide a photothermographic image recording material, i.e., an imaging material that is given an imagewise exposure to light to form a latent image and is then heated overall to form the visible color image.

For photothermographic imaging, a photosensitive silver halide or a component capable of forming a photosensitive silver halide is used in catalytic amounts and in catalytic association with the non-photosensitive organic silver salt. The photosensitive silver halide may be formed simultaneously with the preparation of the organic silver salt, or a compound which forms photosensitive silver halide may be reacted with a previously prepared organic silver salt to convert part of the organic silver salt into silver halide. Also, previously prepared silver halides such as silver chloride, silver bromide, silver iodide, silver bromochloride, silver iodobromochloride, etc. may be mixed with an organic silver salt. For photothermographic systems of the post activatable type, the component capable of forming a photosensitive silver halide upon preliminary heating of the photothermographic layer prior to light exposure may be an organic haloamide or a group IV, V or VI metal halide containing an organic component such as phenyl, substituted phenyl or benzyl groups as described in U.S. Pat. No. 4,347,310.

In the photothermographic materials a reducing agent for silver ions also is employed. The reducing agents used include organic reducing agents which have a reduction ability suitable for the organic silver salt to form a silver image as a result of the catalytic activity of the silver halide in the exposed area when heated. For example, with an organic silver salt such as silver laurate which is relatively easy to reduce, relatively weak reducing agents are preferably employed. On the other hand, with an organic silver salt such as benzotriazole silver salt which is relatively hard to reduce, relatively strong reducing agents are preferably employed. A suitable organic reducing agent or combination thereof may be selected from substituted or unsubstituted bisphenols, substituted or unsubstituted naphthols, mono-, di- or polyhydroxybenzenes, hydroquinone ethers, aseorbic acid or its derivatives, 3-pyrazolidones, pyrazoline-5-ones, aminophenols and p-phenylenediamines. Examples of such reducing agents include 2,2-bis-(4-hydroxyphenyl) propane, 1,1-bis(2-hydroxy-3-t-butyl-5-methylphenyl)methane, 1-naphthol, 1-hydroxy-4-methoxynaphthalene, p-phenylphenol, p-t-butylphenol, catechol, pyrogallol, chlorohydroquinone, 2,5-dimethylhydroquinone, hydroquinone monobenzyl ether, hydroquinone mono-n-hexyl ether, ascorbic acid, ethyl ascorbate, 1-phenyl-3-pyrazolidone, 4-methyl-4-hydroxymethyl-1-phenyl-3-pyrazolidone, 1-phenyl-4-amino-5-pyrazolone, p-aminophenol, 2-methoxy-4-aminophenol and N,N'-diethyl-p-phenylenediamine. Also, reducing agent precursors which, for example, provide a reducing agent upon heating also may be employed. Reducing agents commonly employed with silver behenate because of their light stability and resistance to color change in light include ortho-alkyl- or ortho-aryl-substituted hindered phenols such as 2,6-di-t-butyl-4-methylphenol-2,2'-methylenebis-(4-ethyl-6-t-butylphenol) and bis(3,5-di-t-butyl-4-hydroxyphenyl) ether. The reducing agent or reducing agent precursor preferably is present in the photosensitive layer comprising the organic silver salt and its associated photosensitive silver halide or photosensitive silver halide-forming component.

In addition to the above-described components, these materials may contain conventional modifiers such as an anti-foggant for heat development, e.g., mercuric acetate; a background-darkening preventive agent, e.g., 1,2,3,4-tetra-bromobutane; a matting agent, e.g., silica; a brightening agent, e.g., a stilbene; a filter/antihalation dye, e.g., 1'-ethoxy-3-ethylthia-2'-cyanine tetrafluoroborate; a toning agent, e.g., phthalazinone; and other addenda which are described, for example, in aforementioned Research Disclosure No. 17029 and which are deemed appropriate for a given image recording material.

A variety of exposure means are useful for providing a latent image in the photothermographic material. Typically, a latent image is obtained by imagewise exposure to electromagnetic radiation including visible, ultraviolet and infra red radiation using various light sources such as xenon, tungsten, mercury, iodine or other lamps, lasers, laser diodes, light-emitting diodes and CRT light sources. The exposure should be at least sufficient to provide a developable latent image. Methods for achieving imagewise exposure include photographing with a camera, projective exposure, contact exposure and scanning with a laser beam or other pinpoint source. The use of a laser beam is not only well suited for recording in a scanning mode but by utilizing a highly concentrated beam, photo-energy can be concentrated in a small area so that it is possible to record at high speed and high density. Also, it is a convenient way to record data as a light pattern or a heat pattern in response to transmitted signals such as digitized information and a convenient way of preparing multicolor images by employing a plurality of laser beam sources that emit laser beams of different wavelengths.

After imagewise exposure of the photothermographic material, the dye image can be developed by uniformly heating the photothermographic layer(s) to moderately elevated temperatures for the length of time sufficient to provide the desired dye image. In this embodiment, dye image formation occurs only where development has not taken place, i.e., in areas where Ag+ is still available for reaction with the dye precursor. Preferably, the developed silver is in a low covering power state. Any suitable means can be used as the heating means, for example, a heated platen, a heated drum or roller, or a laser. Also, the material can be passed through a heated atmosphere or heated by high frequency. If desired or appropriate, the photothermographic layer(s) may be heated prior to or during imagewise exposure.

In addition to the layer or layers containing the above-named components, the thermographic and photothermographic image recording elements may contain additional layers, for example, a subbing layer to improve adhesion to the support, interlayers or barrier layers for thermally and chemically isolating the respective organic silver salt/dye precursor layer(s) from each other, infra red absorbing layers, antihalation layers, antistatic layers, back coat layers on the support and other auxiliary layers. For use as magnetic tickets such as commuter tickets and passes, a magnetic recording layer may be carried on the back of the support opposite the imaging layer(s), and for use as adhesive labels, an adhesive layer may be coated on the back of the support and a disposable backing sheet attached to the adhesive layer. As mentioned above, an electroconductive layer may be included and imagewise color formation effected by heat energy in response to an electric signal.

Also, a topcoat or overcoat layer is desirable to reduce abrasion, fingerprints, streaking, gouging, print head build-up, static electricity, improve shelf stability and enhance transparency of the image formed. The overcoat layer may comprise any organic solvent-soluble or water-soluble polymer or resin and preferably contains a fluorochemical surfactant. Also, it may contain ultraviolet absorbers, matting agents, higher fatty acids, waxes and other materials as commonly employed in such layers. Suitable polymers for the overcoat layer include polyvinyl chloride, polyvinyl acetate, copolymers of vinyl chloride and vinyl acetate, polyvinyl butyral, polystyrene, poly-methyl methacrylate, polyurethane, xylene resins, benzyl cellulose ethyl cellulose, cellulose acetate butyrate, cellulose acetate, cellulose triacetate, polyvinylidene chloride, chlorinated polypropylene, polyvinylpyrrolidone, cellulose propionate, polyvinyl formal, cellulose acetate phthalate, polycarbonate and cellulose acetate propionate, etc. Preferred topcoat layers comprise chrome-hardened polyvinyl alcohol, methacrylic acid-diacrylamide copolymers and arylsulfonamideformaldehyde condensation resins containing a fluorocarbon surfactant. Specific examples topcoats are described in detail in U.S. Pat. Nos. 5,278,127; 5,198,406; and (Ser. No. 08/179,516) and are incorporated herein by reference. Furthermore, a washcoat coated over such a topcoat may provided further beneficial results. Such a washcoat is described in Ser. No. 08/193,223, and is incorporated herein by reference.

The various layers of the subject media may be coated on a suitable support by various coating procedures including dip coating, air-knife coating, roll coating, Mayer rod coating, curtain coating, slot method coating, and extrusion coating. If desired, two or more layers can be coated simultaneously. The coating compositions may contain dispersing agents, surfactants, lubricants, plasticizers, defoaming agents, coating aids, pigments, e.g., to provide a white background or a contrasting color for the dye image formed, and so forth. The layers may then be dried at ambient or elevated temperatures provided the temperature is not sufficient to effect premature color formation.

EXAMPLES

To better illustrate the present invention, several Example thermographic image recording materials were prepared and tested as described below. Each Example consisted of three layers coated upon a transparent 2.65 mil polyethylene terephthalate substrate, pretreated with a solvent adherable subcoat (ICI 505, commercially available from ICI Americas, Inc., Wilmington, Del.), using a RK Print Coater (RK Control Coater Model No. K202), followed by hot or warm air drying. It will be appreciated that although a machine coater using a Mayer rod was used for coating, any appropriate coating method could be used, e.g. spray, air knife, gravure, silkscreen, slot method, reverse roll, etc. Layer One was coated using a mixture of ethyl acetate and methanol as solvents. Layer Two was also coated using methyl ethyl ketone as the solvent. Layer Three was coated using water as the solvent. The amount of each component used in each layer was calculated to give, after drying, the approximate coated coverages indicated below. The quantity of silver coated was analytically determined by way of X-ray fluorescence. It is noted that the Examples described herein were prepared individually in the laboratory and are thus subject to more variance than materials prepared on a commercial scale.

| | Coverage (mg/ft$^2$) |
|---|---|
| Layer One: | |
| Polyvinylbutyral | 423 |
| (Butvar B-72, available from Monsanto, St. Louis, Mo.) | |
| 3,5-Dihydroxybenzoic acid | 85 |
| Ethyl Acetate | — |
| Methanol | — |
| Layer Two: | |
| Polyvinylbutyral | 618 |
| (Butvar B-76, available from Monsanto, St. Louis, Mo.) | |
| *Silver behenate dispersion (as silver) | 45 |
| Black Dye Precursor (*see Formula 3 below) | 65 |
| Substituted Purine Compound (see Table 1 below) | 49 |
| Methyl ethyl ketone | — |
| Layer Three: | |
| Nalco 2326 | 100 |
| (5 nm colliodal silica dispersion, 17% T, available from Nalco Chemical Co.) | |
| Cab-O-Sperse A205 | 100 |
| (fumed colloidal silica dispersion having an average particle diameter of 14 nm, available from Cabot Corporation, Cab-O-Sil Division, Tuscola, IL) | |
| Neorez R966 | 31 |
| (Polyurethane latex, 33% total solids (TS), available from ICI Resins, Wilmington, MA) | |
| Hostaflon 5032 | 4 |
| (polytetrafluoroethylene dispersion, 60% TS, available from Hoechst-Celanese, Chatham, NJ) | |
| Zonyl FSN | 5.5 |
| (perfluoroalkyl polyethylene oxide non-ionic surfactant available from DuPont, Wilmington, DE) | |
| Diepoxy RA24C | 25 |
| (1,4-dibutanediol diglycidyl ether, available from Ciba-Geigy Electronic Chemical Group, 3 Skyline Drive, Hawthorne, NY 10532 | |
| Water | — |

*The silver behenate dispersion was prepared according to the procedure described on page 29 of the aforementioned European Patent No. 250,558 of E. J. Dombrowski, Jr. et al.

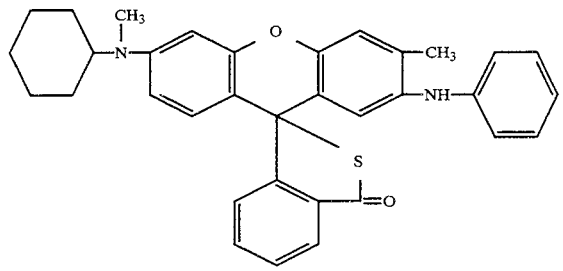

Formula 3
(Black Dye Precursor)

EXAMPLES 1–9

Examples 1–9 were prepared as described above. As a control, Example 1 was prepared without any of the subject substituted purine compounds added thereto. Examples 2–9 each contained approximately 49 mg/ft$^2$ of a substituted purine compound coated in Layer Two. The particular purine compound used for Examples 2–9 is indicated in Table 1 below.

Examples 1–9 were tested for percent gilding by exposing each Example to 10,000 ft.-candles of light (generated by a xenon arc) for seven days at a constant temperature of 85° F. and a relative humidity of 40%. Subsequently, blue light densities for each Example were measured. The blue light density of the Examples closely corresponds to the yellowish-brown color associated with gilding, and thus provides a good measure for gilding. The blue density of the control, Example 1, was assigned a value of 100% gilding and Examples 2–9 were expressed as a percent decrease in gilding, i.e. percent decrease in blue light density, as indicated in Table 1 below.

TABLE 1

| (Example No.) Substituted Purine Compound | % Decrease in Gilding After 7 Days of Exposure |
|---|---|
| (1) No Subst. Purine Compound added | — |
| (2) 9-lauroyl-6-benzylaminopurine | 67 |
| (3) 9-acetyl-6-benzylaminopurine | 52 |
| (4) 9-propionyl-6-benzylaminopurine | 67 |
| (5) 9-butyroyl-6-benzylaminopurine | 65 |
| (6) 6-(N,N-dibenzylamino)purine | 45 |
| (7) 6-(N-methyl-N-benzylamino)purine | 17 |
| (8) 6-(2-pyridylmethylamino)purine | 63 |
| (9) 6-benzylaminopurine | 65 |

As indicated in Table 1, Examples 2–9 all showed reduced gilding when compared to the control, Example 1 which included none of the subject substituted purine compounds.

EXAMPLES 10–15

As a further illustration of the present invention, Examples 10–15 were prepared in the same manner as that described with reference to Examples 1–9; however, Examples 10–15 each included different quantities of 9-lauroyl-6-benzylaminopurine coated therein, (i.e. approximately 0, 8, 16, 33, 50, and 66 mg/ft$^2$, respectively). No other substituted purine compounds were coated in Examples 10–15 other than 9-lauroyl-6-benzylaminopurine. Six samples of each of Examples 10–15 were prepared and individually exposed to 10,000 ft.-candles of light (generated by a xenon arc) at a constant temperature of 85° F. and a relative humidity of 40% for various time periods, (0, 3, 4, 5, 6, and 7 days). After exposure, blue light densities for each sample of each Example were measured and are reported in Table 2 below. Example 10 served as a control as it had no 9-lauroyl-6-benzylaminopurine. The blue densities of the control samples of Example 10 were assigned a value of 100% gilding and Examples 11–15 were expressed as a percent decrease in gilding, i.e. percent decrease in blue light density, and are reported in Table 2 below.

TABLE 2

| Example No. | Coverage (mg/ft²) | Percent Decrease in Gilding at Various Coating Levels of 9-lauroyl-6-benzylaminopurine After Various Time Periods of Exposure | | | | | |
|---|---|---|---|---|---|---|---|
| | | 0 Days | 3 Days | 4 Days | 5 Days | 6 Days | 7 Days |
| 10 | 0 | — | — | — | — | — | — |
| 11 | 8 | — | 18 | 20 | 18 | 21 | 23 |
| 12 | 16 | — | 29 | 30 | 32 | 33 | 35 |
| 13 | 33 | — | 35 | 40 | 41 | 42 | 46 |
| 14 | 50 | — | 35 | 35 | 36 | 42 | 46 |
| 15 | 66 | — | 35 | 40 | 41 | 46 | 54 |

As indicated by the data provided in Table 2, gilding was progressively reduced by the increasing addition of 9-lauroyl-6-benzylaminopurine to the image recording Examples.

Additional samples of Examples 10–15 were prepared as described above and were subsequently imaged using a Model TDU 850 direct thermal printer, available from Raytheon Company, Submarine Signal Division, Portsmouth, R.I. The initial maximum and minimum optical densities for visible, red, green, and blue light were measure for each sample, the results of which are provided in Table 3 below.

TABLE 3

| | | Initial $D_{max}/D_{min}$ Densities of Various Coating Levels of 9-lauroyl- 6-benzylaminopurine | | | |
|---|---|---|---|---|---|
| Example No. | Coverage (mg/ft²) | Visible $D_{max}/D_{min}$ | Red $D_{max}/D_{min}$ | Green $D_{max}/D_{min}$ | Blue $D_{max}/D_{min}$ |
| 10 | 0 | 1.51/.01 | 1.33/.01 | 1.09/.02 | 1.85/.01 |
| 11 | 8 | 1.46/.01 | 1.28/.02 | 1.05/.02 | 1.77/.01 |
| 12 | 16 | 1.37/.01 | 1.20/.02 | 0.98/.02 | 1.67/.01 |
| 13 | 33 | 1.28/.01 | 1.12/.01 | 0.91/.02 | 1.55/.01 |
| 14 | 50 | 1.25/.01 | 1.09/.01 | 0.89/.02 | 1.52/.01 |
| 15 | 66 | 1.15/.01 | 1.00/.01 | 0.82/.02 | 1.41/.00 |

As indicated by the optical density values reported in Table 3, increasing quantities of 9-lauroyl-6-benzylaminopurine reduced the optical densities of the Example materials.

In general, the substituted purine compounds of the present invention may decrease the optical density of recorded images, particularly when used in high quantities. Thus, in addition to considering reduction in gilding, one should further consider any potential reduction in optical density when optimizing a particular system. A balance must often be struck between the reduction of gilding and a reduction of optical density. Routine optimization experiments will provide the necessary information for determining an ideal ratio of individual constituents for a particular system.

Many modification and variations of the present invention are possible in light of the above teachings. It is therefore, to be understood that all matter disclosed in the above description and the accompanying examples should be interpreted as illustrative and not in any way limiting.

We claim:

1. A thermally-processable image recording material comprising a support carrying:
   a di- or triarylmethane thiolactone dye precursor;
   an organic silver salt;
   a binder; and
   a substituted purine compound represented by the formula:

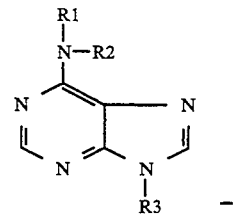

wherein R1, R2, and R3 are substituents which render said purine compound mobile within said image recording material, and provided at least one of R1, R2, and R3 is hydrogen.

2. An image recording material as set forth in claim 1 wherein said substituted purine compound is substantially non-reactive with said binder.

3. An image recording material as set forth in claim 1 wherein R1, R2 and R3 are selected form the groups consisting of: hydrogen, aliphatic alkaryl, and acyl.

4. An image recording material as set forth in claim 3 wherein R1 is selected from hydrogen, alkyl, and alkaryl; R2 is selected from alkaryl; and R3 is selected from hydrogen and acyl.

5. An image recording material as set forth in claim 4 wherein R1 is hydrogen.

6. An image recording material as set forth in claim 5 wherein R2 is benzyl.

7. An image recording material as set forth in claim 6 wherein R3 is an acyl group consisting of a carbonyl group and an alkyl group consisting of 1 to 15 carbon atoms.

8. An image recording material as set forth in claim 1 where said substituted purine compound is selected from the group consisting of:
   (a) 9-lauroyl-6-benzylaminopurine;
   (b) 9-acetyl-6-benzylaminopurine;
   (c) 9-propionyl-6-benzylaminopurine;
   (d) 9-butyroyl-6-benzylaminopurine;
   (e) 6-(N,N-dibenzylamino)purine;
   (f) 6-(N-methyl-N-benzylamino)purine;
   (g) 6-(2-pyridylmethylamino)purine;
   (h) 6-benzylaminopurine; and
   (i) 6-dodecylaminopurine.

9. An image recording material as set forth in claim 1 further including an organic acid material.

10. An image recording material as set forth in claim 9 wherein said organic acid material consists of 3,5-dihydroxybenzoic acid.

11. An image recording material as set forth in claim 1 wherein said silver salt comprises silver behenate.

12. An image recording material as set forth in claim 1 wherein said material is substantially non-photosensitive.

13. An image recording material as set forth in claim 1 further including a photosensitive silver material.

* * * * *